United States Patent [19]

Willis et al.

[11] Patent Number: 5,416,168

[45] Date of Patent: May 16, 1995

[54] PROTECTED FUNCTIONAL INITIATORS FOR MAKING TERMINALLY FUNCTIONALIZED POLYMERS

[75] Inventors: Carl L. Willis, Houston; Robert C. Bening, Katy, both of Tex.

[73] Assignee: Shell Oil Company, Houston, Tex.

[21] Appl. No.: 220,804

[22] Filed: Mar. 31, 1994

[51] Int. Cl.⁶ .................... C08F 36/06; C08F 4/48; C07F 7/04

[52] U.S. Cl. .................... 525/333.2; 525/331.9; 525/338; 525/385; 526/173; 526/178; 526/335; 556/482; 556/465; 502/157; 502/158

[58] Field of Search ............ 526/173, 178, 335; 525/331.9, 333.2, 338, 385; 556/465, 482; 502/157, 158; 260/350 R

[56] References Cited

U.S. PATENT DOCUMENTS

| | | | |
|---|---|---|---|
| 3,324,089 | 6/1967 | Trepka | 526/178 X |
| 3,555,066 | 1/1971 | Le Grow | 526/178 X |
| 3,769,266 | 10/1973 | Nametkin et al. | 526/178 |
| 3,929,850 | 12/1975 | Streck et al. | 526/178 X |
| 5,081,191 | 1/1992 | Quirk | 526/279 X |
| 5,153,291 | 10/1992 | Leitz et al. | 526/279 |
| 5,331,058 | 7/1994 | Shepherd et al. | 526/178 X |
| 5,362,699 | 11/1994 | Shepherd et al. | 502/158 |

FOREIGN PATENT DOCUMENTS 2241239 2/1991 United Kingdom.
9112277 2/1991 WIPO.

Primary Examiner—Fred Teskin
Attorney, Agent, or Firm—Keith M. Tackett

[57] ABSTRACT

The anionic polymerization of unsaturated monomers with functionalized initiators having the structure $R^1R^2R^3Si-O-A'-Li$ is improved when each R is methyl and A' is $-CH_2-C_6H_{10}-CH_2-$ or $-CH_2-CR'R''-CH_2-$ wherein R' is a linear alkyl having from 1 to 10 carbon atoms and R'' is hydrogen or a linear alkyl having from 1 to 10 carbon atoms. This initiator provides process and product advantages over all other known initiators of the same type.

15 Claims, No Drawings

PROTECTED FUNCTIONAL INITIATORS FOR MAKING TERMINALLY FUNCTIONALIZED POLYMERS

FIELD OF THE INVENTION

This invention relates to anionic polymerization of monomers, to functionalized polymers used as components in adhesives, sealants and coatings, and to lithium alkyl reagents used as initiators for the synthesis of these polymers.

BACKGROUND OF THE INVENTION

Anionic polymerization of conjugated dienes with lithium initiators, such as sec-butyllithium, and hydrogenation of residual unsaturation has been described in many references including U.S. Pat. No. Re. 27,145 which teaches a relationship between the amount of 1,2-addition of butadiene and the glass transition temperatures of the hydrogenated butadiene polymers.

The capping of living anionic polymers to form functional end groups is described in U.S. Pat. Nos. 4,417,029, 4,518,753, and 4,753,991. Of particular interest for the present invention are anionic polymers that are capped on one or more ends with hydroxyl, carboxyl, phenol, epoxy, or amine groups.

Anionic polymerization using protected functional initiators having the structure $R^1R^2R^3Si-O-A'-Li$ is described in WO 91/12277 wherein $R^1$, $R^2$, and $R^3$ are preferably alkyl, alkoxy, aryl, or alkaryl groups having from 1 to 10 carbon atoms, and $A'$ is preferably a branched or straight chain bridging group having at least 2 carbon atoms. $R^1$, $R^2$, and $R^3$ are preferably not all $CH_3$. The bridging group ($A'$) is most preferably a straight chain alkyl having from 3 to 10 carbon atoms and is exemplified by the following compound:

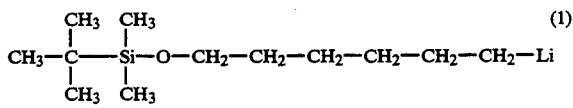

which is readily prepared by lithiation of the reaction product of 1-chloro-6-hydroxy-n-hexane and t-butyldimethylchlorosilane. The use of such an initiator as Structure (1) to polymerize the desired monomer(s), followed by capping to produce the second terminal alcohol group, has several advantages over the preparation of telechelic diols by capping polymers prepared with difunctional initiators such as 1,4-dilithiobutane and lithium naphthalide. In addition to providing the option of polymerizing in non-polar solvents, this route avoids the formation of ionic gels, which are known to occur when diinitiated polymers are capped with reagents such as ethylene oxide, generating the polymeric di-alkoxide. These gels form even in relatively polar solvent mixtures and greatly complicate subsequent processing steps. By capping to produce the alkoxide on only one polymer terminus, these gels are avoided.

The initiator of Structure (1) anionically polymerizes unsaturated monomers like conventional lithium initiators but starts the polymer chain with a t-butyldimethylsiloxy functional group that can be converted to a primary alcohol, which is useful in a variety of subsequent reactions. While it appears that the majority of Structure (1) is active if the initiation step is performed at a low temperature (−5° C.), at slightly higher temperatures, a significant fraction of the initiator charge fails to initiate polymerization; a large portion of the initiator is non-reactive or "dead". Initiation with sec-butyllithium occurs efficiently well above room temperature. Nevertheless, the active portion of the initiator of Structure (1) produces living polymers that can be further end-capped and hydrogenated like conventional anionic polymers.

The initiator of Structure (1) affords a polymer chain having a t-butyldimethylsiloxy functional moiety on the end of it. While that protecting group can be removed (deprotection) to give the desired primary alcohol functionality, it is somewhat difficult to practice and is costly. Deprotection of polymers of this type requires contacting with a molar excess (5X stoichiometry) of a strong organic acid, such as methanesulfonic acid, and a compatabilizing cosolvent such as isopropanol (about 20% wt). This mixture is then stirred at elevated temperatures (about 50° C.) until the polymer is deprotected (several hours depending on the specific initiator that is used). When the polymer has been deprotected, it is then necessary to neutralize the acidic hydrolysis catalyst, wash out the spent acid salt, and distill out the compatabilizing cosolvent. These additional steps add time and cost to the process. A functional initiator that contained a protecting group that was easier to remove would be advantaged in processing efficiency.

The polymers derived from initiators of the type described in Structure (1) tend to have a non-uniform microstructure. In the early stages of the polymerization of butadiene using an initiator of this type, 1,4-addition of monomer is the dominant mode of incorporation of butadiene. Even when a solvent system that is high in a microstructure modifier is employed, such as 10% wt diethylether in cyclohexane, the 1,4-addition of butadiene is over 70%. As the polymer grows longer and the C—Li end of the chain distances itself from the t-butyldimethylsiloxy functional end, this effect dissipates and the microstructure of the added units are controlled by the nature of the solvent; at 10% wt diethyl ether in cyclohexane, it would be about 50–60% wt 1,4-addition of butadiene. The adverse effect of this variance in microstructure is manifest in the saturated, hydrogenated, polymer. The segment of the polymer having a linear microstructure, high 1,4-addition of butadiene, becomes a polyethylene segment on hydrogenation and tends to have polyethylene-like crystallinity. This crystallinity tends to increase the viscosity of liquid polymers near room temperature and, in the extreme, may induce the sample to solidify. For the preparation of low viscosity, hydrogenated, functional polymers, an initiator is needed that has protected functionality and allows the preparation of a butadiene polymer that has a uniform microstructure that can be controlled at intermediate levels of 1,4-addition.

It is an object of the present invention to provide improved protected functional initiators that operate efficiently (with a minimum of dead initiator) at economical temperatures. These initiators should operate to afford a butadiene polymer of uniform and controlled microstructure and should be deprotected under mild and low cost conditions.

SUMMARY OF THE INVENTION

The present invention is the discovery that lithium compounds having the structure:

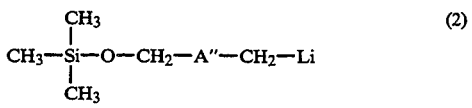

wherein A" is cyclohexyl or —CR'R"—, wherein R' is a linear alkyl having from 1 to 10 carbon atoms and R" is hydrogen or a linear alkyl having from 1 to 10 carbon atoms, initiate polymerization of anionic polymers at surprisingly higher polymerization temperatures with surprisingly lower amounts of dead initiator (higher efficiency) than similar initiators having linear bridging groups connecting the oxygen and the lithium. The initiators of Structure (2) are also suprisingly easier to deprotect than similar initiators having branched alkyls bonded to the silicon. The polymers produced by these initiators are readily endcapped and hydrogenated to form anionic polymers having one or more terminal functional groups under commercially-attractive conditions.

DETAILED DESCRIPTION OF THE INVENTION

The polymerization of unsaturated monomers with functionalized initiators having the structure $R^1R^2R^3Si$—O—A'—Li is described in WO 91/12277 wherein $R^1$, $R^2$, and $R^3$ are preferably alkyl, alkoxy, aryl, or alkaryl groups having from 1 to 10 carbon atoms, and A' is preferably a branched or straight chain bridging group having at least 2 carbon atoms, preferably linear alkyls having from 3 to 10 carbon atoms.

The present invention is the discovery that lithium initiators having the structure:

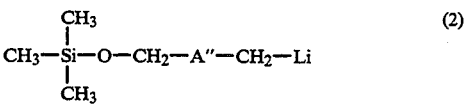

wherein A" is cyclohexyl or —CR'R"—, wherein R' is a linear alkyl having from 1 to 10 carbon atoms and R" is hydrogen or a linear alkyl having from 1 to 10 carbon atoms, preferably A" is —CR'R"— wherein R" is methyl, initiate polymerization of anionic polymers at surprisingly higher polymerization temperatures with surprisingly lower amounts of dead initiator (higher efficiency) than similar initiators having linear bridging groups connecting the oxygen and the lithium. These initiators are surprisingly effective at affording diene polymers having a uniform and controllable microstructure by comparison to similar initiators having a branched alkyl moiety bonded to the silicon center. The initiator of structure (2) prepares homopolymers of butadiene which have a uniform distribution of 1,2-addition across the polymer chain when the amount of 1,2-addition is between 5 and 95% wt, more preferably between 30 to 70% wt.

The efficiency of initiators of this type is readily determined by a variety of analytical methods. In living polymerizations, each mole of active initiator is expected to start one mole of polymer, so that the average molecular weight of the resulting polymer can be predicted from the following relationship:

$$MW_{ave} = (m_{mono}/m_{init})(MW_{mono}) + MW_{init} + MW_{cap} \quad (1)$$

where:
- $m_{mono}$ = moles of monomer
- $m_{init}$ = moles of initiator
- $MW_{mono}$ = molecular weight of the monomer
- $MW_{init}$ = MW of the fragment of the initiator that is incorporated into the polymer chain
- $MW_{cap}$ = MW of the fragment of the capping reagent that is incorporated into the polymer chain If a fraction of the initiator charge fails to start polymer, the resulting product will be higher in molecular weight than predicted by equation (1). So long as that fraction remains inactive throughout the polymerization, the molecular weight distribution (MWD) will remain narrow and monodisperse, typical of a living polymerization having a faster rate of initiation than of propagation. In practice, molecular weights are often somewhat larger than predicted by equation (1) due to inactivation of a small fraction of the initiator charge by protic impurities present in monomers, solvents, etc.

The initiators of the present invention are similar to s-butyllithium with regard to economical operating temperature and low amounts of dead initiator and a uniform, controlled level of 1,2-addition of diene in the product polymer. However the initiators of the invention have the advantage of placing a silyl ether group at the start of the polymer chain which serves as a "masked" or "protected" alcohol, capable of conversion to a primary, neopentyl-type alcohol group after polymerization is completed by reaction with acids or bases under mild, low cost conditions or as described in WO 91/12277. The polymer chains may be terminated, endcapped, or coupled by conventional means to end the polymerization and provide one or more terminal functional groups on linear or branched polymers containing polymerized conjugated dienes.

While the initiator of Structure (1) would, after polymerization and deprotection, afford a polymer having primary alcohol functionality, a polymer having primary alcohol functionality of the neopentyl-type should have improved thermal stability and condensation polymers derived from it should have improved hydrolytic stability. The improved thermal stability of neopentyl alcohol and the hydrolytic characteristics of its derivatives are summarized in Advanced Organic Chemistry, Third Edition, by J. March, John Wiley & Sons, New York (1985) (see particularly pp. 285, 299, 390, 514, 944, 955, 959, and references therein). It is reasonable that polymers having this special structure would have similarly improved properties.

The lithium initiator process is well known as described in U.S. Pat. No. 4,039,593 and U.S. Pat. No. Re. 27,145 which descriptions are incorporated herein by reference. Typical living polymer structures that can be made with lithium initiators such as Structure (2) include:

X—B—Li
X—B/A—Li
X—A—B—Li
X—B—A—Li
X—B—B/A—Li
X—B/A—B—Li
X—A—B—A—Li wherein B represents polymerized units of one or more conjugated diene hydrocarbons, A represents polymerized units of one or more vinyl aromatic compounds, B/A represents random polymerized units of the conjugated diene hydrocarbons and the vinyl aromatic monomers, and X is the residue of the lithium initiator. The living polymers are terminated as linear polymers, coupled to form branched polymers, or cappped to form additional functional groups by conventional means such as addition of methanol, silicon tetrachloride, divinylbenzene, or ethylene oxide. In the present invention, X is a trimethylsilyl ether group and cleavage of the trimethylsilyl ether leaves a neopentyl-like primary alcohol group in this position. These primary alcohols have different reactivity than other primary alcohol groups which will lead to different rates of reaction for the chain ends with diisocyanates and dicarboxylic acids and the like. This difference in reactivity rates could be very useful in designing materials where stepwise polymerization is desired.

The initiators of the present invention are very active at room temperature and polymerization is preferably initiated at a temperature from 15° C. to 60° C., most preferably from 30° C. to 40° C. It is generally advisable to keep the polymerization temperature below about 100° C.; above this temperature, side reactions that change microstructure and limit capping efficiency may become important. Polymerizations can be carried out over a range of solids levels, preferably from about 5% to about 80% wt polymer, most preferably from about 10% to about 40% wt. For high solids polymerizations, it is preferable to add the monomer in increments to avoid exceeding the desired polymerization temperature. If the initiator is to be added to the full monomer charge, it is preferable to run the polymerization between 10% and 20% wt solids.

When the conjugated diene is 1,3-butadiene and when the conjugated diene polymer will be hydrogenated, the anionic polymerization of the conjugated diene hydrocarbons is typically controlled with structure modifiers such as diethyl ether or glyme (1,2-diethoxyethane) to obtain the desired amount of 1,2-addition. As described in U.S. Pat. No. Re. 27,145 which is incorporated by reference herein, the level of 1,2-addition of a butadiene polymer or copolymer can greatly affect the rheology and elastomeric properties of the polymer after hydrogenation. The hydrogenated polymers exhibit improved heat stability and weatherability in the final, adhesive, sealant or coating.

The 1,2-addition of 1,3-butadiene polymers having terminal functional groups influences the viscosity of the polymers as described in more detail below. A 1,2-addition of about 40% is achieved during polymerization at 50° C. with about 6% by volume of diethyl ether or about 1000 ppm of glyme. Generally, vinyl contents in this range are desirable if the product is to be hydrogenated, while low vinyl contents are preferred if the polymer is to be used in its unsaturated form.

Anionic polymerization is often terminated by addition of water to remove the lithium as lithium hydroxide (LiOH) or by addition of an alcohol (ROH) to remove the lithium as a lithium alkoxide (LiOR). Polymers prepared from initiators of the present invention and terminated in this way will be monohydroxy functional materials (mono-ols) after removal of the trimethylsilyl protecting group. To prepare polymers having an additional terminal functional groups, the living polymer chains are preferably terminated with hydroxyl (—OH), carboxyl (—CO$_2$H), phenol (ArOH), epoxy, or amine groups by reaction with ethylene oxide (—OH), oxetane (—OH), 2,2-dimethyloxetane (—OH), carbon dioxide (—CO$_2$H), a protected hydroxystyrene monomer (ArOH), ethylene oxide plus epichlorohydrin (epoxy), or the aziridine compounds listed in U.S. Pat. No. 4,791,174 (amine). For the preparation of telechelic diols, the preferred process is to terminate with 1–10 equivalents, most preferably 1–2 equivalents, of ethylene oxide at 30° C.–50° C. This reaction is quite rapid; reaction times from 5 to 30 minutes yield acceptable results.

The termination step or neutralization step can result in release of fine particles of lithium bases as described in U.S. Pat. No. 5,166,277 which is incorporated by reference herein. The lithium bases may interfere with hydrogenation of the polymer and preferably are removed, especially if the hydrogenation is to be carried out at high solids.

Termination with carbon dioxide results in carboxylate salt groups that reduce hydrogenation catalyst activity as described in U.S. Pat. No. 4,970,254 which disclosure is incorporated by reference herein. Improved hydrogenation is obtained by converting the carboxylate salt groups to ester groups prior to hydrogenation and then reconverting to carboxylate salt or carboxylic acid groups after hydrogenation.

Hydrogenation of at least 90%, preferably at least 95%, of the unsaturation in low molecular weight butadiene polymers is achieved with nickel catalysts as described in U.S. Pat. No. Re. 27,145 and U.S. Pat. No. 4,970,254 and U.S. patent application Ser. No. 07/785715 now U.S. Pat. No. 5,166,277 which are incorporated by reference herein. The preferred nickel catalyst is a mixture of nickel 2-ethylhexanoate and triethylaluminum described in more detail in the examples. It is preferable to extract the nickel catalyst after hydrogenation by stirring the polymer solution with aqueous phosphoric acid (2–30 percent by weight), at a volume ratio of about 0.5 parts aqueous acid to 1 part polymer solution, at about 50° C. for 30–60 minutes while sparging with a mixture of oxygen in nitrogen. This step is also described in more detail in the examples.

Saturated or unsaturated conjugated diene polymers having one or more terminal functional group selected from hydroxyl, carboxyl, phenol, epoxy, and amine groups can be used without solvents when the viscosity of the polymer is less than about 500 poise at mixing and application temperature. Linear hydrogenated butadiene or isoprene polymers having two terminal hydroxyl groups per molecule and lower viscosity than 500 poise at mixing and application temperatures are produced by limiting the peak molecular weight to a range from about 500 to 20,000 and by limiting the 1,2-addition of hydrogenated butadiene to an amount between 30% and 70%, preferably between 40% to 60%.

After polymerization and, optionally, hydrogenation and washing of the polymer, the trimethylsilyl group at the front of the polymer chain is removed to generate the desired primary, neopentyl-type hydroxyl functional group. This step is often referred to as deprotection. A variety of processes for removal of the silyl protecting group are known; for a review, see T. W. Greene, "Protective Groups in Organic Synthesis", J. Wiley and Sons, New York, 1981. Deprotection preferably involves easily handled, relatively low toxicity, inexpensive reagents and mild, low cost process conditions. Reaction with tetrabutylammonium fluoride in THF, as described in WO 91 112277, is disadvantaged due to the high cost and toxicity of the reagents. In a preferred process, the trimethylsilyl group is removed after hydrogenation and during the aqueous acid wash for removal of the spent Ni/Al hydrogenation catalyst.

This technique avoids the cost associated with a separate process step for deprotection. For the preparation of an unsaturated polymer where hydrogenation catalyst extraction is not required, contacting the polymer cement with a dilute aqueous acid or dilute aqueous base solution is preferred for deprotection.

For some applications, such as coatings prepared by baked cures of the polymer with amino resins in the presence of a strong organic acid catalyst, it may be preferable to use the polymer in its "protected" form. The viscosity of the protected polymer is lower and conditions such as those described above should accomplish the deprotection (generate the alcohol) during the cure.

The conjugated diene polymers produced as described above have the conventional utilities for terminally functionalized polymers of such as forming adhesives, coatings, and sealants. Additionally, the polymers may be used to modify polyurethanes, polyesters, polyamides, polycarbonates, and epoxy resins.

DETAILED DESCRIPTION OF PREFERRED EMBODIMENTS

The most preferred process uses the initiator having the following structure:

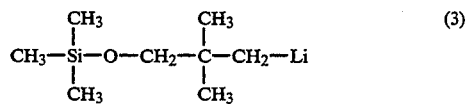

(3-lithio-2,2-dimethyl-1-trimethylsilyloxypropane) to produce dihydroxylated 1,3-butadiene polymers having a peak molecular weight from 500 to 200,000, most preferably from 500 to 20,000. The dihydroxylated polymers can be unsaturated with 1,2-addition from 5% to 95% or hydrogenated with 1,2-addition from 30% to 70%. The polymers preferably have from 1.75 to 2.0, most preferably from 1.95 to 2.0, terminal hydroxyl groups per molecule.

After polymerization of the desired amount of 1,3-butadiene, the living polymer is capped with ethylene oxide and reacted with methanol to give a terminal primary alcohol group. The silyl group is then converted to a primary, neopentyl-type hydroxyl group by reaction with dilute aqueous acid or dilute aqueous base.

The preferred polymers of the present invention are useful in adhesives (including pressure sensitive adhesives, contact adhesives, laminating adhesives and assembly adhesives), sealants (such as urethane architectural sealants, etc.), coatings (such as topcoats for automotive, epoxy primers for metal, polyester coil coatings, alkyd maintenance coatings, etc.), films (such as those requiring heat and solvent resistance), molded and extruded thermoplastic and thermoset parts (for example thermoplastic injection molded polyurethane rollers or reaction injection molded thermoset auto bumper, facie, etc.).

A composition of the instant invention may contain plasticizers, such as rubber extending plasticizers, or compounding oils or organic or inorganic pigments and dyes. Rubber compounding oils are well-known in the art and include both high saturates content oils and high aromatics content oils. Preferred plasticizers are highly saturated oils, e.g. Tufflo ® 6056 and 6204 oil made by Arco and process oils, e.g. Shellflex ® 371 oil made by Shell. The amounts of rubber compounding oil employed in the invention composition can vary from 0 to about 500 phr, preferably between about 0 to about 100 phr, and most preferably between about 0 and about 60 phr.

Optional components of the present invention are stabilizers which inhibit or retard heat degradation, oxidation, skin formation and color formation. Stabilizers are typically added to the commercially available compounds in order to protect the polymers against heat degradation and oxidation during the preparation, use and high temperature storage of the composition.

Various types of fillers and pigments can be included in the coating or sealant formulation. This is especially true for exterior coatings or sealants in which fillers are added not only to create the desired appeal but also to improve the performance of the coatings or sealant such as its weatherability. A wide variety of fillers can be used. Suitable fillers include calcium carbonate, clays, talcs, silica, zinc oxide, titanium dioxide and the like. The amount of filler usually is in the range of 0 to about 65% w based on the solvent free portion of the formulation depending on the type of filler used and the application for which the coating or sealant is intended. An especially preferred filler is titanium dioxide.

The dihydroxylated conjugated diene polymers of the present invention may also be blended with other polymers to improve their impact strength and/or flexibility. Such polymers are generally condensation polymers including polyamides, polyurethanes, vinyl alcohol polymers, vinyl ester polymers, polysulfones, polycarbonates and polyesters, including those, like polyacetones, which have a recurring ester linkage in the molecule, and those, like polyalkylene arylates, including polyalkylene terephthalates, having a structure formed by polycondensation of a dicarboxylic acid with a glycol. The blends may be made in the reactor or in a post compounding step.

The present invention is further described by the following examples which include the best mode known to Applicant for making a dihydroxylated, saturated polybutadiene (EB Diol). The examples are not intended to limit the present invention to specific embodiments although each example may support a separate claim which Applicant asserts to be a patentable invention.

The peak molecular weights were measured using gel permeation chromatography (GPC) calibrated with polybutadiene standards having known peak molecular weights. The solvent for the GPC analyses was tetrahydrofuran.

The 1,2-additions of polybutadiene were measured by $^{13}C$ NMR in chloroform solution.

Initiator Synthesis

EXAMPLE 1

The initiator of structure (3), designated PFI10, was prepared using the procedures broadly described in WO 91 112277. The hydroxyl functionality in 2,2-dimethyl-3-chloropropanol was protected by reaction with trimethylsilyl chloride. A solution of trimethylsilyl chloride (27.16 g, 0.25 mol) in dry cyclohexane (150 g) was treated with 20.4 g of imidazole (0.30 mol) under an argon atmosphere. The resulting slurry was stirred vigorously at room temperature as 2,2-dimethyl-3-chloropropanol (30.93 g, 0.25 mol) was added slowly to the mixture. The rate of addition was controlled to keep the reaction temperature below 40° C. The resulting slurry was filtered affording a clear solution of the desired 1-trimethylsilyloxy-2,2-dimethyl-3-chloropropane. Analysis using a Gas Chromatography-Mass Spectroscopy (GC-MS) technique found essentially no side products. The trimethylsilyl protected adduct was obtained in quantitative yield. A repeat of this experiment gave similar results.

The trimethylsilyl adduct of 2,2-dimethyl-3-chloropropanol was lithiated affording the desired lithium alkyl. For this experiment, Li metal was obtained as a dispersion (0.5% wt Na) in mineral oil (30% wt Li) and the dispersion was washed repeatedly, under an argon atmosphere with dry cyclohexane to remove the mineral oil carrier. A slurry of the freshly washed Li metal (28 g, 4.03 mol) in cyclohexane (180 g) was contacted with vigorous stirring with a portion of the cyclohexane solution (73.07 g of solution) of the trimethylsilyl adduct (about 24 g of adduct, about 0.12 mol of adduct) prepared as described above. The rate of addition of the chloropropane reagent was controlled to keep the temperature of the reaction solution below 40° C. When addition of the trimethylsilyl adduct of 2,2-dimethyl-3-chloropropanol was complete, the resulting slurry was filtered (5 micron filter) affording a clear solution of 3-lithio-2,2-dimethyl-1-trimethylsilyloxypropane in cyclohexane. An aliquot of the product solution was titrated with diphenylacetic acid according to the procedure of Korfron and Baclawski (J. Org. Chem., 41, 1879(1976)). This analysis, which is specific for C-Li moieties, found the present reagent to have a lithium alkyl concentration of 0,217M (4.65% wt). A repeat of this lithiation reaction afforded a reagent having a lithium alkyl concentration of 0.22M (4.74wt %). A third replicate experiment included additional cyclohexane which gave a reagent solution having a lithium alkyl concentration of 0.095M (2.03% wt).

EXAMPLE 2

Using the procedure described in Example 1, the hydroxyl functionality in 2,2-dimethyl-3-bromopropanol (83.52 g, 0.5 mol) was protected by reaction with trimethylsilyl chloride (54.32 g, 0.5 mol) in the presence of an excess of imidazole (41.8 g, 0.61 mol). The product was isolated and analyzed as described in Example 1. The trimethylsilyl protected adduct was obtained in quantitative yield.

Using the procedure described in Example 1, the solution of the trimethylsilyl adduct of 2,2-dimethyl-3-bromopropanol (31.38 g, 0.13 mol) was reacted with an excess of Li metal (about 35 g, about 5.04 mol) in cyclohexane (102 g). The product was isolated and analyzed as described in Example 2. A solution of 3-lithio-2,2-dimethyl-1-trimethylsilyloxypropane in cyclohexane (0.13M, 2.72% wt RLi) was obtained.

EXAMPLE 3 (COMPARISON)

Using the procedure described in Example 1, PFI11 was prepared wherein the hydroxyl functionality in 3-chloropropanol (47.27 g, 0.5 mol) was protected by reaction with trimethylsilyl chloride (54.32 g, 0.5 mol) in the presence of an excess of imidazole (40 g, 0.587 mol). The product was isolated and analyzed as described in Example 1. The trimethylsilyl protected adduct was obtained in quantitative yield.

Using the procedure described in Example 1, the solution of the trimethylsilyl adduct of 3-chloropropanol (19.77 g, 0.118 mol) was reacted with an excess of Li metal (about 28 g, about 4.03 mol) in cyclohexane (100 g). The product was isolated and analyzed as described in Example 2. A solution of 3-lithio-1-trimethylsilyloxypropane in cyclohexane (0.101M, 1.8% wt RLi) was obtained.

EXAMPLE 4 (COMPARISON)

Additional comparison initiators, designated PFI2 and PFI3, were prepared in dry cyclohexane by reaction of 2,2-dimethyl-3-chloropropanol and 3-chloropropanol (respectively) with t-butyldimethylsilyl chloride (TBDMS-Cl) in the presence of imidazole, followed by reaction with lithium metal, as broadly described in WO 91 112277. The concentration of active lithium alkyl was determined by titration with diphenylacetic acid, as described above (W. G. Korfron and L. M. Baclawski *J. Org. Chem*, 41(10), 1879 (1976)).

Polymerization

EXAMPLE 5

Reaction of the lithium initiator of structure (3) with butadiene effectively initiated polymerization and reaction of the living polymer product with ethylene oxide afforded, after isolation, a high yield of a telechelic polybutadienyl diol.

A solution of the 3-lithio-2,2-dimethyl-1-trimethylsilyloxypropane (RLi)(157.85 g of solution, 4.74% wt RLi, 0,045 mol RLi) in cyclohexane, prepared as described in Example 1, was added, under argon, to a solution of polymerization grade butadiene monomer (180 g, 3.33 mol) in a mixed cyclohexane/diethyl ether (202 g cyclohexane/60 g diethyl ether) solvent with vigorous stirring in a steel autoclave. Not all of the monomer was present in the reactor at the start of polymerization as a portion of the monomer was held in reserve and added to the reactor at a rate that allowed control of the reaction temperature during the exothermic polymerization reaction. Polymerization was initiated at 15° C. and the resulting exothermic reaction raised the solution temperature to 21.7° C.

Immediately after the addition of the lithium initiator to the reactor when polymerization had just begun, an aliquot of the living polymer solution was removed for analysis and quenched immediately by addition of an excess of MeOH. (Just Initiated Sample). The remainder of the solution was allowed to react to essentially complete consumption of the butadiene (85 min). An aliquot of the living polymer solution was taken from the reactor for analysis and quenched immediately by addition of an excess of MeOH. (Complete Polymerization Sample). The bulk of the solution which contained a living butadiene polymer having a trimethylsilyloxy moiety on one end of the polymer chain was treated with an excess of ethylene oxide (3.4 g, 0.077 mol). The ethoxylation reaction was allowed to proceed for 60 min at 40° C. The cement was treated with 4 g of methanol. An aliquot of the resulting polymer cement was removed for analysis (EO Capped Sample). The bulk of the reaction product was reserved for an hydrogenation experiment which is described in Example 8.

The sample collected just after initiation of butadiene polymerization (Just Initiated Sample) was found to have a number average molecular weight ($MW_N$) of 514 (as measured by a Carbon-13 Nuclear Magnetic Resonance (NMR) method which compares the ratio of the carbon signal that is attributed to the alkyl segment of the initiator to the total carbon signal for the sample). Analysis of this sample for vinyl content, also using an NMR technique, found that 45.5% wt of the butadiene had added by 1,2-polymerization affording pendant vinyl unsaturation with the remainder added by 1,4-polymerization giving enchained unsaturation species. When the sample that was collected after complete polymerization of the butadiene was analyzed using the same methods, the molecular weight (as measured by a gel permeation chromatography (GPC) technique) was found to be 4997 ($MW_N$) and the 1,2-polymerization content was 45.5% wt. As both of these samples have the same 1,2-polymerization levels, it is clear that the microstructure of the polymer prepared using the trimethylsilyloxy protected initiator is uniform throughout the polymerization process, a preferred result, and is intermediate in vinyl content (45.5% wt) when about 10% wt diethyl ether is present in the polymerization solvent. As the targetted MW for this polymerization was 4000 and the observed MW for the completely polymerized sample was 4997, it is clear that 80% of the lithium alkyl added to the reactor was effective in initiating polymerization with the remainder being lost to deactivation processes ("die-out") prior to or during polymerization.

These results show that the initiators of Structure (2) are effective for butadiene polymerization at commercially useful temperatures. Further, these results show that these initiators prepare functionalized butadiene polymers having a uniform microstructure. A uniform and intermediate microstructure is preferred during butadiene polymerization for avoiding crystallinity problems (polyethylene segments) when the polymer is hydrogenated.

The EO Capped Sample was concentrated at 50° C. under reduced pressure to afford a sample for High Pressure Liquid Chromatography (HPLC) analysis (a 250 mm×4.6 mm, 5 micro DIOL phase column, using a stepped heptane/THF solvent gradient with an evaporative light scattering detector). This method of analysis found principally a butadiene polymer having 2 hydroxyl functional sites per molecule (a telechelic polybutadiene diol) with a trace (less than 2% wt) of polymer having 1 hydroxyl functional site per molecule (a polybutadiene having an hydroxyl functional group on only one end of the chain); there was no evidence for TMS capped polymer in this sample. Apparently, the TMS protecting group was removed under the conditions used for concentrating the samples (methanolic LiOMe at 50° C. for a few minutes). This is a very mild deprotection condition. The 3-lithio-2,2-dimethyl-1-trimethylsilyloxypropane initiator is preferred for affording a polymer having masked hydroxyl functionality that is readily deprotected under mild, basic conditions.

EXAMPLE 6

The polymerization process described above was repeated using another aliquot of 3-lithio-2,2-dimethyl-1-trimethylsilyloxypropane (89.39 g of solution, 4.15 g RLi, 0.025 mol RLi) and 100 g (1.85 mol) of butadiene in the mixed cyclohexane (710 g)/diethyl ether (100 g) solvent. Analysis of the polymer before EO addition using the methods described above found $MW_N=5149$ for an initiator efficiency of 78%. In this instance, the sample taken after EO addition was repeatedly (4×) washed with an excess of aqueous phosphoric acid (10% wt acid) to remove basic lithium species from the sample prior to concentration of the sample for HPLC analysis. The sample was concentrated as noted above and analyzed. As observed in Example 5, no TMS capped polymer was found; a telechelic polybutadiene diol was isolated in high yield with a trace of the monohydroxyl polymer being present. Mild phosphoric acid treatment also gave the desired, deprotected, functional polymer. This experiment has shown that 3-lithio-2,2-dimethyl-1-trimethylsilyloxypropane is a preferred initiator for butadiene polymerization because of its high efficiency for initiation of polymerization and for the ease of deprotection of the functional polymer product under mildly acidic conditions.

EXAMPLE 7

A third polymerization experiment under similar conditions used 265.65 g of a solution (2.74% wt RLi) of 3-lithio-2,2-dimethyl-1-trimethylsilyloxypropane (0,044 mol RLi), 175 g (3.24 mol) of butadiene, and the same cyclohexane (85 g)/diethyl ether (59 g) solvent. For this experiment, initiator efficiency was 107% (this value being greater that 100% is a reflection on the accuracy of the experiment; an initiator efficiency greater than 100% is not possible for this chemistry). The sample taken after EO addition was deprotected on contact with wet THF for a few minutes. Again, a polymer prepared using this initiator was converted to the desired hydroxyl modified moiety under very mild conditions.

EXAMPLE 8

An EO capped butadiene polymer prepared using 3-lithio-2,2-dimethyl-1-trimethylsilyloxypropane as the initiator was hydrogenated using a Ni/Al technique; the saturated polymer product was deprotected under the conditions used to extract the spent hydrogenation catalyst affording the desired hydrogenated, telechelic, polybutadiene diol. The hydrogenation catalyst (Ni/Al) for this experiment was prepared in advance by combining nickel 2-ethylhexanoate with triethylaluminum in cyclohexane in amounts sufficient to give a ratio of 2.5 moles of Al to 1 mole of Ni. A butadiene polymer ($MW_N=4997$) cement (30% wt polymer) prepared as described in Example 5 using 3-lithio-2,2-dimethyl-1-trimethylsilyloxypropane as the polymerization initiator was transferred after the EO capping step to a 500 cc steel autoclave and sparged with hydrogen at 40° C. The reactor was then pressured up to 700 psig with hydrogen and the Ni/Al catalyst added in aliquots to control the resulting exothermic reaction. Sufficient Ni/Al catalyst was eventually added to bring the total solution concentration of Ni to 100 ppm. After 2 hr of hydrogenation, an aliquot of the product was removed and analyzed for unreacted C=C moieties using an ozone titration technique. This analysis found that over 97% of the starting polybutadienyl unsaturation had been hydrogenated. A portion of this sample was repeatedly extracted with an aqueous phosphoric (10% wt acid) solution in the presence of air. This technique oxidized the reduced metal species and extracted the metal salts into the aqueous phase. The organic phase was concentrated and analyzed using the HPLC method described in Example 5. This analysis found the desired saturated, telechelic, polybutadiene diol with a trace of the saturated, monohydroxyl functional polymer being present as the side product. The TMS protecting group having been removed, apparently, during the aqueous workup of the product.

EXAMPLE 9

Using the procedure described in Example 5, the solution of 3-lithio-2,2-dimethyl-1-trimethylsilyloxypropane in cyclohexane prepared in Example 1 was used to initiate the anionic polymerization of butadiene. As described in Example 5, the living polymer was capped by reaction with EO, isolated and analyzed. For this experiment, the initiator efficiency was 108%; a telechelic, polybutadienyl diol was obtained having $MW_N=3700$.

As shown by the following comparisons, the initiators described in Examples 1 and 2 have excellent efficiency for the initiation of butadiene polymerization at commercially useful temperatures and afford functional polymers having primary, neopentyl type hydroxyl moieties and polymers that have a uniform distribution of 1,2-polymerization and are easily deprotected under mild conditions.

EXAMPLE 10 (COMPARISON)

Using the procedure described in Example 5, the solution of 3-lithio-1-trimethylsilyloxypropane in cyclohexane prepared in Example 3 was used to initiate the anionic polymerization of butadiene. As described in Example 5, the living polymer was capped by reaction with EO, isolated and analyzed. For this experiment, the initiator efficiency was 30%; a telechelic, polybutadienyl diol was obtained having $MW_N=13,170$ (target $MW_N=4000$). Clearly the absence of branching on the bridging group between the silicon and the lithium centers resulted in an inferior polymerization initiator having a remarkably poor efficiency for the initiation of butadiene polymerization. At commercially useful temperatures most of this lithium alkyl failed to initiate the growth of a polymer chain.

Although this lithium alkyl did not afford a good initiator due to poor initiation efficiency, analysis of the product as described in Example 5 showed that the product had a uniform microstructure. The 1,2-polymerization of butadiene content in the Just Initiated Sample was 41.6% wt and that of the final product was 42.4% wt. The use of the trimethylsilyl protecting group allowed the preparation of a butadiene polymer having a uniform and controllable microstructure.

EXAMPLE 11 (COMPARISON)

A hydrogenated linear butadiene polymer having about two terminal hydroxyl groups per molecule, a peak molecular weight of 3,900, an average repeat unit structure consistent with 40% 1,2-addition of butadiene, and a residual unsaturation of 0.17 meq/g (98.9% hydrogenated) is prepared with PFI3 of Example 4 as described below: 675 g. (12.5 moles) of butadiene, 450 g. of diethyl ether and 3375 g. of cyclohexane were charged into a 2 gal. stainless steel autoclave. The reactor was heated to 40° C. and 280 g. of a 10.9% wt. solution of PFI3 in cyclohexane (0.169 moles) was added; the heat of reaction increased the reactor temperature to about 45° C. After about 9 minutes, the reaction temperature was increased to about 50° C. and polymerization was allowed to continue for about 40 minutes. After 40 minutes, the reactor was cooled to about 40° C. and 31 g. (4 equivalents) of ethylene oxide was added. After 30 minutes, 6 g. (1.1 equivalents) of methanol was added. GPC Analysis indicated a molecular weight of 3,900 amu., in good agreement with the targeted value of 4,000 amu. Analysis of this sample by Carbon-13 Nuclear Magnetic Resonance (NMR) indicates that, on average, 40% wt of the butadiene had added by 1,2-polymerization affording pendant vinyl unsaturation with the remainder added by 1,4-polymerization giving enchained unsaturation species. The bulk of the reaction product was and reserved for an hydrogenation experiment which is described in Example 12.

EXAMPLE 12 (COMPARISON)

The polymer cement from Example 11 was charged into a 3 gal. high-pressure stainless steel autoclave, diluted to 9.5% solids by the addition of 2,597 g. of cyclohexane, and heated to 40° C. The reactor was sparged with hydrogen at a rate of about 0.6 SCFM, while maintaining a pressure of 800 psi. 70.8 mls. of a 6700 ppm (Ni) Solution of Ni/Al catalyst was charged to the reactor, resulting in an immediate exothermic reaction. The catalyst was prepared in advance by reacting nickel 2-ethylhexanoate with triethylaluminum in cyclohexane in amounts sufficient to give a ratio of 2.0 moles of aluminum to 1 mole of nickel. After peaking at about 90° C., the temperature decreased and was held at about 70° C. Analysis for residual unsaturation (ozone titration) indicated about 99% conversion after 120 minutes. The catalyst was extracted by washing the cement with two 500 ml. aliqouts of 20% aqueous phosphoric acid.

In contrast to the previous examples, the t-butyldimethylsilyl ether group was not cleaved during the acid wash. Hydrolysis of the t-butyldimethylsilyl ether protecting group was performed as follows: A solution containing 70 g. of water and 81 g. of anhydrous methanesulfonic acid (5 moles per mole of polymer) in 1050 g. of isopropanol was added to the washed polymer cement (5500 g.). The resulting slightly hazy solution was stirred for 2 hours at about 50° C. The sample was washed with one aliquot of 0.1 N aqueous sodium hydroxide and two aliquots of DI water (about 5.4 liters each); the pH of the aqueous phase after the second water wash was about 7. The polymer solvent was removed in a rotary evaporator. The sample was analyzed by High Pressure Liquid Chromatography (HPLC) and $^{13}C$ NMR, to determine the relative amounts of the desired dihydroxy material (diol), mono-hydroxy material (either capped with EO but not deprotected or deprotected but terminated by protic impurities) and non-functional material (protected—no EO incorporated). The HPLC separation was accomplished with a 250 mm×4.6 mm 5 micron DIOL phase column using a stepped heptane/tetrahydrofuran gradient. An evaporative light scattering detector is used to quantify the sample. These techniques indicate 98% and 97% conversion to the di-hydroxy product, respectively.

The neat polymer was observed to be a clear, colorless, moderately viscous liquid at temperatures at or above about 50° C., however, on cooling to room temperature, the product became hazy and substantially more viscous. This transition was reversible, suggesting that the haziness and increased viscosity was a result of crystallization. Analysis by Differential Scanning Calorimetry (DSC) confirmed this result; a broad endotherm was observed in the temperature range over which clearing occurs. The pronounced crystallinity observed in this sample was unexpected for hydrogenation of a polymer with an average 1,2-addition frequency of 40%, suggesting the possibility that the rate of 1,2 addition may have changed during the course of polymerization, resulting in "runs" substantially higher in the 1,4 addition—product, which form the bulk of the crystallizable material on hydrogenation. Such "tapering" is known to occur if the reaction temperature exceeds about 90° C. during the polymerization, but this was not observed during this polymerization.

EXAMPLE 13 (COMPARISON)

The following experiment was performed in order to determine if the 1,2 addition frequency varies during the course of the polymerization of butadiene with PFI3 in cylohexane/diethyl ether solvent systems: Butadiene (100 g.) was added to a 90/10 mixture of cyclohexane/diethyl ether (900 g. total) in a 2 liter glass autoclave (Büchi). The quantity of initiator solution expected to produce an approximately 4,000 molecular weight polymer was added to the monomer solution at 20° C.–23° C. and then the temperature was increased to 40° C. over about a 10 minute period, by setting the temperature of the circulating bath to 43.5° C.; temperature control is provided by circulating water from a temperature-controlled circulating bath, through a concentric jacket. The polymerization was sufficiently exothermic to increase the reactor temperature to at least 48° C. The polymerization was allowed to proceed at about 50° C. for about 45 minutes before about 2 equivalents ethylene oxide (EO) was added to generate the terminal hydroxyl group. After about 30 minutes, the reaction was terminated with about 1.1 equivalents of methanol.

Samples were collected at several time points after initiation of butadiene polymerization, corresponding to conversions between about 13% and 100%. The average vinyl content was determined for each sample by NMR, as described previously; these results are summarized below:

| % Conversion | Molecular Weight (NMR) | % 1,2 Repeat Units |
|---|---|---|
| 13 | 500 | 26 |
| 24 | 900 | 35 |
| 52 | 1980 | 40 |
| 75 | 2850 | 41 |
| 100 | 3800 | 40 |

The microstructure of this polymer prepared using the t-butyldimethylsilyloxy protected initiator is non-uniform, with 1,4 addition being much more frequent early in the polymerization, which leads to undesired crystallinity when the polymer is hydrogenated.

EXAMPLE 14 (COMPARISON)

A linear butadiene polymer having about two terminal hydroxyl group per molecule, a peak molecular weight of 4,400, and an average repeat unit structure consistent with 40% 1,2-addition of butadiene, was prepared as described below, using PFI2, the t-butyldimethylsilyl—protected analog of the initiator of Example 1: Butadiene was polymerized with PFI2 in a glass autoclave, as described in Example 13. Ethylene oxide was added following polymerization of the butadiene, and the polymerization was terminated with methanol, resulting in a polymer with the silyl ether group (protected alcohol) at one end, a primary alcohol group at the other.

Hydrolysis of the silyl ether functional group of polymers prepared from this initiator was found to be very difficult; an hydrolysis attempted according to the procedure of Example 12 resulted in little conversion to the alcohol. The following conditions were required to generate the desired diol product in satisfactory yield: Ten equivalents of MSA was added to the washed solution, along with sufficient IPA and water as to afford a concentration of 42 weight percent IPA and about 0.6 weight percent water in the reaction mixture. This solution was heated at 50° C. for a total of 19 hours; samples were taken at 1, 2 and 3 hours. The final product was washed with aqueous base, and then water, and then finished in a rotary evaporator, as described above. HPLC analysis of each sample indicated that the ultimate conversion, to about 98% diol, had been achieved in 3 hours. Clearly, removal of the protecting group from a polymer prepared with an initiator that possesses both a branched bridging alkyl (A') group and a bulky t-butyl group on silicon is very difficult.

EXAMPLE 15 (COMPARISON)

Tables 1–6 summarize the results of polymerizations with initiators possessing a variety of bridging alkyl groups structures, in which the alcohol functionality is protected using the t-butyldimethylsilyl group. Initiation and polymerization was generally carried out at or above room temperature and examples are provided where polymerizations were carried out with and without the ether cosolvent. The last column tabulates "initiation efficiency", which is a measure of how well equation (1) predicts the observed molecular weight. It is readily apparent from these tables that the initiation efficiency of about 80 to 100% achieved by PFI10 (3-lithio-2,2-dimethyl-1-trimethylsilyloxypropane) is as good as, or better than most initiators in which the hydroxyl functionality is protected using the t-butyldimethylsilyl group.

TABLE 1

PFI1-Initiated Polymer (n-hexyl) (Comparison)

| # | Calc. MW | Capping Reagent | GPC MW | Initiation Efficiency[10] |
|---|---|---|---|---|
| 1A[1] | 5,270 | oxetane | 9,960 | 53% |
| 1B[2] | 6,400 | EO | 12,280 | 52% |
| 1C[2] | 4,320 | EO | 15,430 | 28% |
| 1D[3] | 4,290[6] | oxetane | 13,800 | 31% |
| 1E[3] | 1,490[7] | oxetane | 3,900 | 38% |
| 1F[3] | 4,290[8] | oxetane | 15,700 | 27% |
| 1G[3] | 4,460 | oxetane | 15,400 | 29% |
| 1H[4] | 4,290 | oxetane | 16,400 | 26% |
| 1I[4] | 3,880[9] | oxetane | 16,800 | 23% |

[1]titrated initiator conc. 21% wt.; polymerized at 6.5% solids.
[2]titrated initiator conc. 12.5% wt.
[3]titrated initiator conc. 13.1% wt.
[4]titrated initiator conc. 12.7% wt.
[5]polymerized at 7.3% solids.
[6]isoprene, no ether.
[7]isoprene, 10% ether.
[8]Initiate at 10° C., 1 hr., no ether.
[9]Initiated at 30° C.
[10]($MW_{target}/MW_{GPC}$) × 100

TABLE 2

PFI2-Initiated Polymer (Comparison)

| # | Calc. MW | Capping Reagent | GPC MW | Initiation Efficiency[7] |
|---|---|---|---|---|
| 2A[1] | 4,880 | oxetane | 4,800 | 102%[6] |
| 2B[1] | 4,690 | EO | 5,000 | 94% |
| 2C[1] | 5,140[4] | EO | 5,500 | 93% |
| 2D[2] | 5,280[4] | oxetane | 5,700 | 93% |
| 2E[3] | 4,090 | oxetane | 4,160 | 98% |
| 2F[3] | 1,810 | oxetane | 1,770[5] | 102%[6] |
| 2G[3] | 1,560 | oxetane | 1,470 | 106%[6] |

TABLE 2-continued

PFI2-Initiated Polymer (Comparison)

| # | Calc. MW | Capping Reagent | GPC MW | Initiation Efficiency[7] |
|---|---|---|---|---|
| 2H[1] | 4,000 | EO | 4,400 | 91% |

[1]titrated initiator conc. 11.4% wt.
[2]titrated initiator conc. 9.6% wt.
[3]titrated initiator conc. 13.5% wt.
[4]isoprene, no ether.
[5]Polymerized at 6.5% solids.
[6]Values greater than 100% reflect the level of accuracy in MW determination.
[7]$(MW_{target}/MW_{GPC}) \times 100$.

TABLE 3

PFI3-Initiated Polymer (n-propyl) (Comparison)

| # | Calc. MW | Capping Reagent | GPC MW | Initiation Efficiency[7] |
|---|---|---|---|---|
| 3A[1] | 4,210 | oxetane | 4,200 | 100% |
| 3B[1,3] | 3,940 | oxetane | 5,800 | 68% |
| 3C[1,3] | 3,980 | oxetane | 6,100 | 65% |
| 3D[1] | 3,920 | oxetane | 4,200 | 93% |
| 3E[2] | 4,050 | oxetane | 4,300 | 94% |
| 3F[2] | 1,540 | oxetane | 1,800 | 86% |
| 3G[2] | 4,000 | EO | 5,600[4] | 71% |
| 3H[2] | 3,830 | EO | 4,700 | 82% |
| 3I[2] | 1,500 | H | 1,900 | 79% |
| 3J[5] | 4,000 | EO | 3,900 | 102%[6] |

[1]titrated initiator conc. 15.0% wt.
[2]titrated initiator conc. 14.3% wt.
[3]Reaction temperature maintained below 55° C.
[4]polymerized at 15% solids.
[5]butadiene, no ether.
[6]Values greater than 100% reflect the level of accuracy in MW determination.
[7]$(MW_{target}/MW_{GPC}) \times 100$.

TABLE 4

PFI4-Initiated Polymer (n-buty) (Comparison)

| # | Calc. MW | Capping Reagent | GPC MW | Initiation Efficiency[4] |
|---|---|---|---|---|
| 4A[1,2] | 4,000 | EO | 24,000 | 17% |
| 4B[1,3] | 3,990 | EO | 11,700 | 34% |

[1]titrated initiator conc. 10.4% wt.
[2]initiation temperature = 20° C., 10% solids.
[3]initiation temperature = 30° C., 13.5% solids.
[4]$(MW_{target}/MW_{GPC}) \times 100$.

TABLE 5

PFI5-Initiated Polymer (n-pentyl) (Comparison)

| # | Calc. MW | Capping Reagent | GPC MW | Initiation Efficiency[5] |
|---|---|---|---|---|
| 5A[1,2] | 4,190 | EO | 6,600 | 63% |
| 5B[1,3] | 4,270 | EO | 8,000 | 53% |
| 5C[1,4] | 4,060 | EO | 9,500 | 43% |
| 5D[1,2] | 4,000 | EO | 9,800 | 41% |

[1]titrated initiator conc. 17.5% wt.
[2]initiation temperature = 30° C., 15% solids.
[3]initiation temperature = 25° C., 10% solids.
[4]initiation temperature = 40° C., 10% solids.
[5]$(MW_{target}/MW_{GPC}) \times 100$.

TABLE 6

PFI6-Initiated Polymer (n-octyl) (Comparison)

| # | Target MW | Capping Reagent | GPC MW | Initiation Efficiency[5] |
|---|---|---|---|---|
| 6A[1,2] | 4,000 | EO | 4,600 | 87% |
| 6B[1,3] | 4,000 | EO | 4,600 | 87% |
| 6C[1,4] | 4,000 | EO | 4,400 | 91% |

[1]titrated initiator conc. 19.1% wt.
[2]initiation temperature = 30° C., 15% solids.
[3]initiation temperature = 30° C., 10% solids.
[4]initiation temperature = 20° C., 10% solids.
[5]$(MW_{target}/MW_{GPC}) \times 100$.

We claim:

1. A process for making functionalized polymers, comprising the steps of:
   initiating polymerization of an unsaturated monomer at a temperature from 15° C. to 60° C. with a lithium initiator having the structure

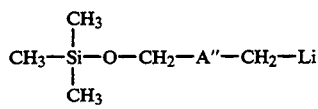

wherein A″ is cyclohexyl or —CR′R″—, wherein R′ is a linear alkyl having from 1 to 10 carbon atoms and R″ is hydrogen or a linear alkyl having from 1 to 10 carbon atoms; and
   recovering a linear or branched polymer having one or more terminal functional groups.

2. The process of claim 1, further comprising the step of reacting the polymer with ethylene oxide prior to recovering the polymer.

3. The process of claim 1, wherein the unsaturated monomer is butadiene.

4. The process of claim 3, further comprising the step of hydrogenating the polymerized butadiene.

5. The process of claim 1 wherein A″ is —CR′R″— and R″ is methyl.

6. The process of claim 5 wherein R′ is methyl.

7. A functionalized polymer produced by a process comprising the steps of:
   initiating polymerization of an unsaturated monomer at a temperature from 15° C. to 60° C. with a lithium initiator having the structure

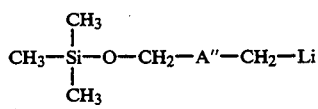

wherein A″ is cyclohexyl or —CR′R″—, wherein R′ is a linear alkyl having from 1 to 10 carbon atoms and R″ is hydrogen or a linear alkyl having from 1 to 10 carbon atoms; and
   recovering a linear or branched polymer having one or more terminal functional groups.

8. The polymer of claim 7, further comprising the step of reacting the polymer with ethylene oxide prior to recovering the polymer.

9. The polymer of claim 8, wherein the unsaturated monomer is butadiene.

10. The polymer of claim 9, further comprising the step of hydrogenating the polymerized butadiene.

11. The polymer of claim 7 wherein A″ is —CR′R″— and R″ is methyl.

12. The polymer of claim 11 wherein R′ is methyl.

13. A lithium compound for making functionalized polymers, having the structure:

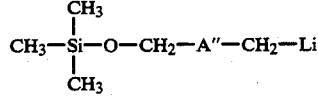

wherein A″ is cyclohexyl or —CR′R″—, wherein R′ is a linear alkyl having from 1 to 10 carbon atoms and R″ is hydrogen or a linear alkyl having from 1 to 10 carbon atoms.

14. The compound of claim 13 wherein A″ is —CR′R″ and R″ is methyl.

15. The compound of claim 14 wherein R′ is methyl.

* * * * *